United States Patent [19]

Spinelli et al.

[11] Patent Number: 5,466,245
[45] Date of Patent: Nov. 14, 1995

[54] METHOD AND APPARATUS TO CONTINUOUSLY OPTIMIZE THE A-V DELAY IN A DUAL CHAMBER PACEMAKER

[75] Inventors: Julio C. Spinelli, Shoreview; Jan P. Heemels, Minneapolis, both of Minn.

[73] Assignee: Cardiac Pacemakers, Inc., St. Paul, Minn.

[21] Appl. No.: 339,815

[22] Filed: Nov. 15, 1994

[51] Int. Cl.[6] .................................................. A61N 1/368
[52] U.S. Cl. .................................................. 607/17; 607/9
[58] Field of Search ................................. 607/17, 9, 16, 607/27, 25; 128/703, 706

[56] References Cited

U.S. PATENT DOCUMENTS

| 4,303,075 | 12/1981 | Heilman et al. . |
| 4,674,518 | 6/1987 | Salo . |
| 4,686,987 | 8/1987 | Salo et al. . |
| 4,832,038 | 5/1989 | Arai et al. ............................... 128/702 |
| 5,024,222 | 6/1991 | Thacker . |
| 5,312,452 | 5/1994 | Salo .......................................... 607/17 |
| 5,334,222 | 8/1994 | Salo et al. ................................ 607/17 |

OTHER PUBLICATIONS

Perry, J. G., Nanda, N. C., "Evaluation of Pacemaker Dynamics by Doppler Echocardiography" Journal of Electrophysiology, 1(2):173–188, 1987.
Wish M., Fletcher, R. D., "Optimal Left Atrioventricular Sequence In Dual Chamber Pacing–Limitations of Programmed A–V Interval" Journal American College of Cardiology, 3:507A, 1984 (abstract).
Julio C. Spinelli, Max E. Valentinuzzi, "Stroke Volume In The Dog: Measurements by the Impedance Technique and Thermodilution" Medical Progress through Technology 10:45–53, 1983.
Julio C. Spinelli, Max E. Valentinuzzi, "High–sensitivity, high–linearity, low–leak, self–balanced cardiograph", Medical Progress through Technology, 9:239–245, 1983.

Primary Examiner—William E. Kamm
Assistant Examiner—Kennedy J. Schaetzle
Attorney, Agent, or Firm—Haugen and Nikolai

[57] ABSTRACT

A DDD-type cardiac pacemaker having a microprocessor-based controller is programmed to automatically determine and utilize and optimize A-V delay for the patient in whom the device is implanted. The microprocessor-based controller periodically changes the A-V delay and then computes heart rate variability over an insuing predetermined period. The particular A-V delay value associated with the minimum heart rate variability index is determined to be the optimum. Heart rate variability may be determined by performing a power spectrum analysis on cyclic variations in R-R intervals, preferably using a FFT signal processing chip, or by a time domain analysis based upon the standard deviation of R-R intervals during a prescribed period of time and a calculated value of respiratory sinus arrhythmia. The apparatus is also operative to optimize the A-V delay interval following a change in the pacing mode of the DDD-type pacemaker.

22 Claims, 2 Drawing Sheets

METHOD AND APPARATUS TO CONTINUOUSLY OPTIMIZE THE A-V DELAY IN A DUAL CHAMBER PACEMAKER

BACKGROUND OF THE INVENTION

I. Field of the Invention

This invention relates generally to implantable cardiac rhythm management apparatus, and more particularly to such an apparatus and method that automatically establishes an optimum A-V delay interval for a DDD pacemaker.

II. Discussion of the Prior Art

With present day state-of-the-art, programmable, implantable pacemakers, a cardiologist is able to periodically program into the device an A-V delay value that yields an optimum stroke volume by, for example, using external instrumentation like a Doppler flow meter to measure changes in cardiac output as the A-V delay interval for the pacer is systematically changed. Such an approach at optimization is not only time consuming, but may only be appropriate for the patient at the time that the testing and setting of the A-V delay interval is made. In the literature, the optimum value of the A-V delay has generally been defined as that delay value that produces the maximum stroke volume for a fixed heart rate or the maximum cardiac output for a sinus node driven heart rate. For patients suffering from congestive heart failure (CHF), the A-V delay interval can be varied over a wide range without any measurable change in stroke volume. Studies which we have conducted suggest that CHF patients would have a very narrow range for the optimum A-V delay, meaning that small deviations, e.g., only 10 milliseconds, from the optimum can diminish the clinical benefit obtained using DDD pacing.

To explain these apparently contradictory results, one needs to understand that the body regulates the heart directly, such as by changing the heart rate and contractility, through the sympathetic and parasympathetic tones and indirectly through the load. A major role in this regulatory scheme is played by the baroreceptors. The baroreceptors, located in the major thoracic arteries, are pressoreceptors that compare the arterial pressure with a reference value. If the pressure exceeds the reference value, the baroreceptors emit signals that enter the tractus solitarius of the medulla. Secondary signals also inhibit the vasoconstrictor center of the medulla and excite the vagal center. The net effects are vasodilation of the veins and the arterioles throughout the peripheral circulatory system and decreased heart rate and strength of heart contractions. Therefore, excitation of the baroreceptors by pressure in the arteries reflexly causes the arterial pressure to decrease because of both a decrease in peripheral resistance and a decrease in cardiac output. Conversely, low pressure (a pressure lower than the reference value) has opposite effects, reflexly causing the pressure to rise back toward normal.

When it is recognized that A-V delay only effects the timing of the atrial contraction in relationship with the next following ventricular contraction, a change in A-V delay will only change the hemodynamic performance of the heart as a mechanical pump. If a patient is not already using his/her compensation mechanisms, a less than optimal A-V delay would mechanically impair the pump performance. If this impairment is of a sufficient degree to produce a pressure change, the baroreceptor mechanism can come into play to increase the contractility and cancel the hemodynamic effect that the less than optimum A-V delay would have produced. The more seriously that the heart of a CHF patient is impaired, the more his/her organism will use these compensation mechanisms and the less his/her regulatory system will be able to compensate for a less than optimum A-V delay. This tends to explain the finding of very narrow ranges of optimum A-V delays in sick patients.

In 1981, M. Heilman and M. Mirowski proposed a method and apparatus for maximizing stroke volume through atrioventricular pacing using an implanted cardioverter/pacer which accomplishes A-V sequential pacing with an A-V delay tailored to the particular patient. One of its disadvantages is that it attempted to control the A-V delay on a beat-by-beat basis, measuring the beat-by-beat stroke volume. However, the beat-by-beat variation of the peak-to-peak impedance proved not to be a reliable enough approach to be used as a parameter to determine the A-V delay, since its amplitude is going to be affected by motion artifacts, electric noise, etc. Another disadvantage of that method and apparatus is that it does not provide any way to identify the origin of the stroke volume change, which could have been produced by a change in heart rate, by a change in the systemic or peripheral resistance or by a change in the venous return. Also, any affect of the A-V delay on the stroke volume tends to be masked by physiologic feedback mechanisms that try to maintain cardiac output constant so as to satisfy metabolic needs.

We hypothesize that the clinical findings, obtained while using stroke volume as the variable to optimize A-V delay, have been affected by the feedback mechanisms that the body normally applies to maintain the supply of blood during load changes. If this hypothesis is correct, the A-V delay changes operate to modify the pump performance, but its actual output has been kept constant by the feedback introduced by the sympathetic and parasympathetic systems. In patients with a very narrow range for the optimum A-V delay, it is possible that their feedback mechanisms were either impaired or already used and, therefore, unable to completely compensate for the effect produced in the pump efficiency by the A-V delay.

SUMMARY OF THE INVENTION

The method and apparatus to continuously optimize the A-V delay in accordance with the present invention is based upon the fact that for optimum A-V delay, the ratio between the activity of the sympathetic system and the activity of the parasympathetic system should be a minimum. This ratio is referred to as the heart rate variability index ($HRV_i$).

The system of the present invention comprises a conventional implantable DDD or DDDR cardiac rhythm management device having a telemetry capability, plus added software or firmware to perform an analysis of the heart rate variability. In particular, the system comprises a means for sensing both atrial and ventricular depolarization signals and a means for stimulating ventricular tissue all under the control of a microprocessor-based controller that is programmed to determine a $HRV_i$ during a predetermined time interval. The microprocessor-based controller responds to the detection of an atrial depolarization signal and establishes an optimum A-V delay interval corresponding to a minimum $HRV_i$. The controller then causes this optimum A-V delay to be used in timing the occurrence of a ventricular stimulating pulse following the sensing of an immediately preceding atrial depolarization signal.

To compute the $HRV_i$, cyclic variations in the R-R interval are determined during a defined interval and then a frequency domain (power spectrum) analysis is performed. The power spectrum analysis decomposes the heart rate signal into its frequency components and quantifies them in terms of their relative intensity, i e., "power". It is found that the power spectrum includes a low frequency band and a high frequency band. $HRV_i$ is the ratio of low frequency power to high frequency power.

It is accordingly a principal object of the present invention to provide in a single system the ability for automatically programming an optimum A-V delay interval and a pacing mode for a DDD pacemaker with respect to a minimum ratio between sympathetic and parasympathetic tones.

Another object of the invention is to provide an apparatus and method for automatically programming an optimum A-V delay interval and pacing mode for a patient that does not require external equipment, such as a Doppler flow meter, since the hardware and software embedded in the implantable cardiac rhythm management device is itself sufficient to achieve the optimization.

Yet another object of the invention is to provide a cardiac rhythm management device for use by patients suffering from CHF that has the capability of maintaining an optimum A-V delay even when the mode of pacing is changed.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
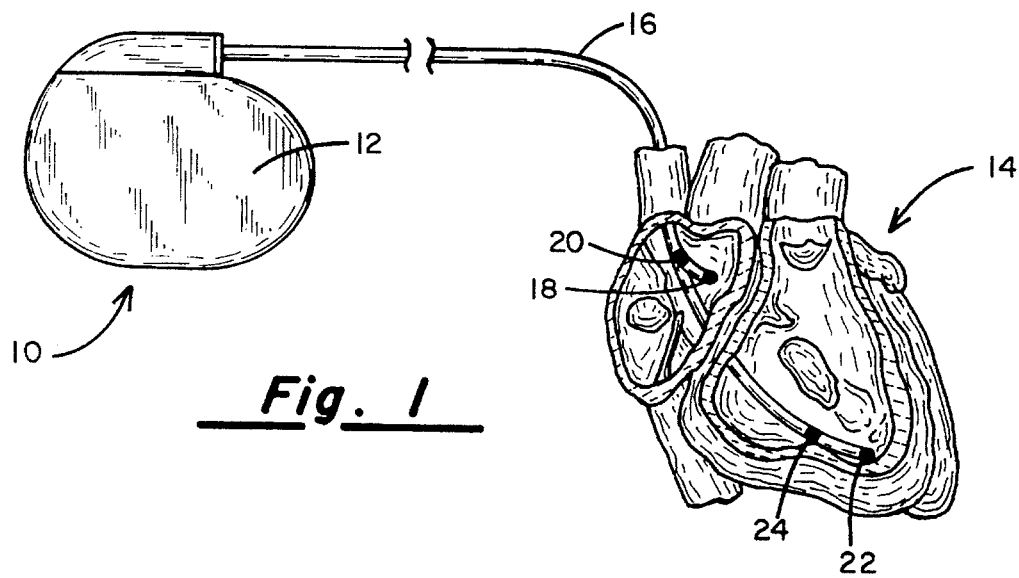
FIG. 1 illustrates an implantable cardiac rhythm management device coupled to a patient's heart via appropriate sensing/pacing leads.

Referring first to FIG. 1, there is indicated generally by numeral 10 a cardiac rhythm management device, here shown as a DDD bradycardia pacemaker 12, which is operatively coupled to a patient's heart 14 by means of a conventional pacing lead 16 having atrial pacing and sensing electrodes 18 and 20 and ventricular pacing and sensing electrodes 22 and 24.

Figure 2:
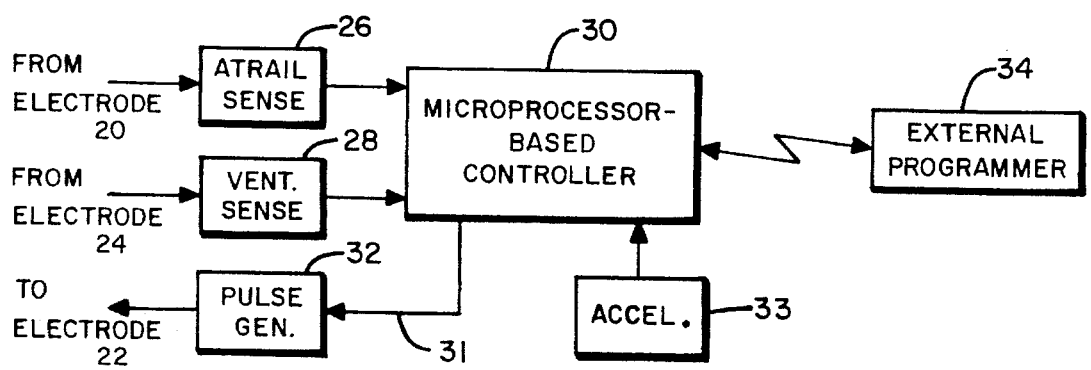
FIG. 2 is a general block diagram of the circuitry incorporated in the cardiac rhythm management device of FIG. 1.

Referring now to FIG. 2, the atrial sensing electrode 20 disposed in the right atrium of the heart 14 is coupled by a wire in the lead 16 to an atrial sense amplifier 26 and, similarly, the ventricular sensing electrode 24 is connected by a wire in the lead 16 to a ventricular sense amplifier 28 contained within the pacemaker 12. Thus, when the SA node in the right atrium depolarizes, the resulting signal is picked up by the atrial sense amplifier 26 and applied to the microprocessor-based controller 30. Ventricular depolarization signal (R-Waves) are likewise amplified and applied as an input to the microprocessor-based controller 30.

As will be more fully explained, the algorithm employed is operative at a time that the patient is at rest or asleep and to establish that fact, motion indicative of activity is sensed by an accelerometer 33 and that information, coupled with heart rate, is used to establish the "at rest" state.

The microprocessor-based controller is connected in controlling relationship to a pulse generator 32 to cause a ventricular stimulating pulse to be applied, via lead 16 and the tip electrode 22, to tissue located proximate the apex of the right ventricle to initiate ventricular depolarization that spreads as a wave across both the right and left ventricles. The microprocessor-based controller 30 not only controls the rate at which cardiac stimulating pulses are produced, but also the timing thereof relative to a preceding atrial depolarization signal to thereby define the A-V interval. An external programmer 34 is arranged to send radio frequency signals transcutaneously to the implanted pacemaker and also to receive signals originating in the pacemaker. In this fashion, a physician is capable of programming such parameters as rate, pulse width, pulse amplitude, sensitivity, etc., in a fashion known in the art. The external programmer may also be used to receive signals and to pass them on to an external monitor (not shown).

Figure 3:
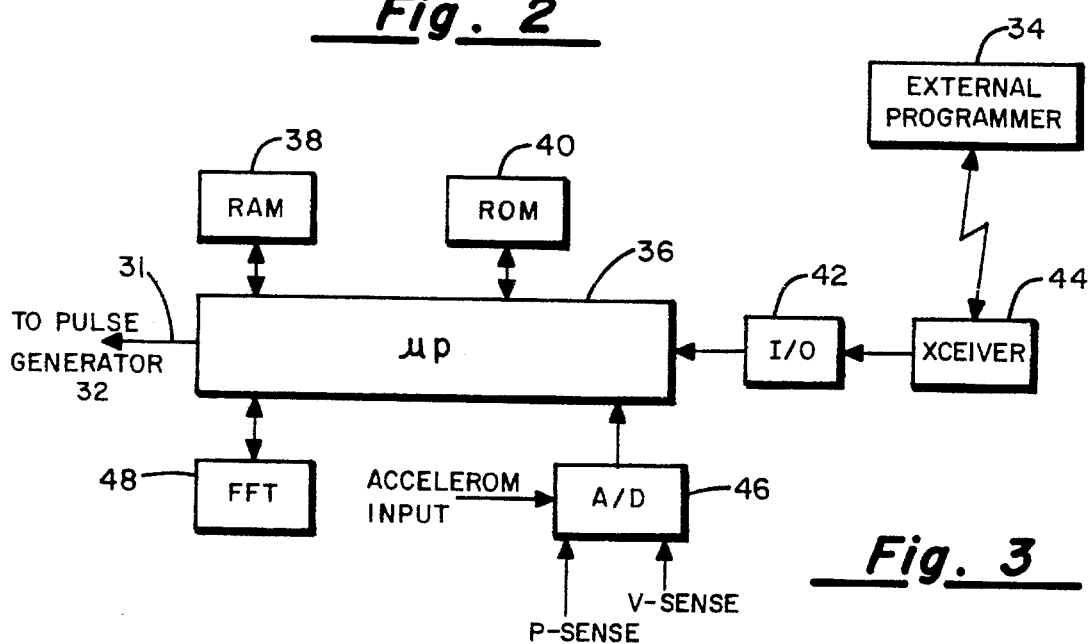
FIG. 3 is a more detailed block diagram of the implementation of the microprocessor-based controller shown in FIG. 2.

Referring next to FIG. 3, there is shown a more detailed block diagram of the microprocessor-based controller 30. It is seen to include a microprocessor chip 36 and associated RAM and ROM memory modules 38 and 40 connected to the microprocessor by an address bus and a data bus. Generally speaking, and without limitation, the RAM memory 38 is capable of storing data words/operands used in the execution of one or more programs that may be stored in the ROM memory 40. An input/output interface module 42 is used to couple a transceiver 44 to the microprocessor 36 whereby information can be exchanged between the microprocessor 36 and an external programmer 34, as previously described.

An analog-to-digital (A/D) converter 46 receives inputs from the sense amplifiers 26 and 28 of FIG. 2 and is effective to digitize the analog voltage signals for further processing by the microprocessor 36.

The microprocessor 36 provides a control output on line 31 to the pulse generator 32.

As will be explained in greater detail below, the microprocessor 36 is also coupled to a Fast Fourier Transform chip 48 which is used in forming the heart rate variability index, $HRV_i$. In a paper entitled "Heart Rate Variability—Frequency Domain Analysis" by Zsolt Ori et al. appearing in *Cardiology Clinics*, vol. 10, No. 3, August 1992, there are described, in detail methods of computing the heart rate a variability by determining the power in a low frequency portion of the power spectrum and dividing it by the high frequency power in that same power spectrum. This ratio corresponds to the ratio of sympathetic tone to parasympathetic tone. An Appendix to the Ori et al. paper provides the mathematical formula for estimating the energy distribution over frequency using the classical power spectrum analysis employing the Fast Fourier Transform (FFT). Further information on measuring heart rate variability is contained in a paper by Kleiger et al. entitled "Stability Over Time of Variables Measuring Heart Rate Variability in Normal Subjects", *Am J Cardiol*, 68:626–630, 1991. The FFT chip 48 is especially adapted to providing frequency domain analysis and when applied to the cyclic changes in the sinus rate over time, $HRV_i$ is computed. A paper entitled "Heart Rate Variability as a Prognostic Tool in Cardiology" by Maximilian Moser et al., *Circulation*, Vol. 90, No. 2, August 1994, describes a method in which respiratory sinus arrhythmia (RSA) is used to measure parasympathetic tone and because the standard deviation (SD) of R-R intervals over a predetermined period of time is a measure of sympathetic and parasympathetic tone, the heart rate variability index ($HRV_i$) can be estimated as:

$$HRV_i = SD/RSA.$$

Figure 4:
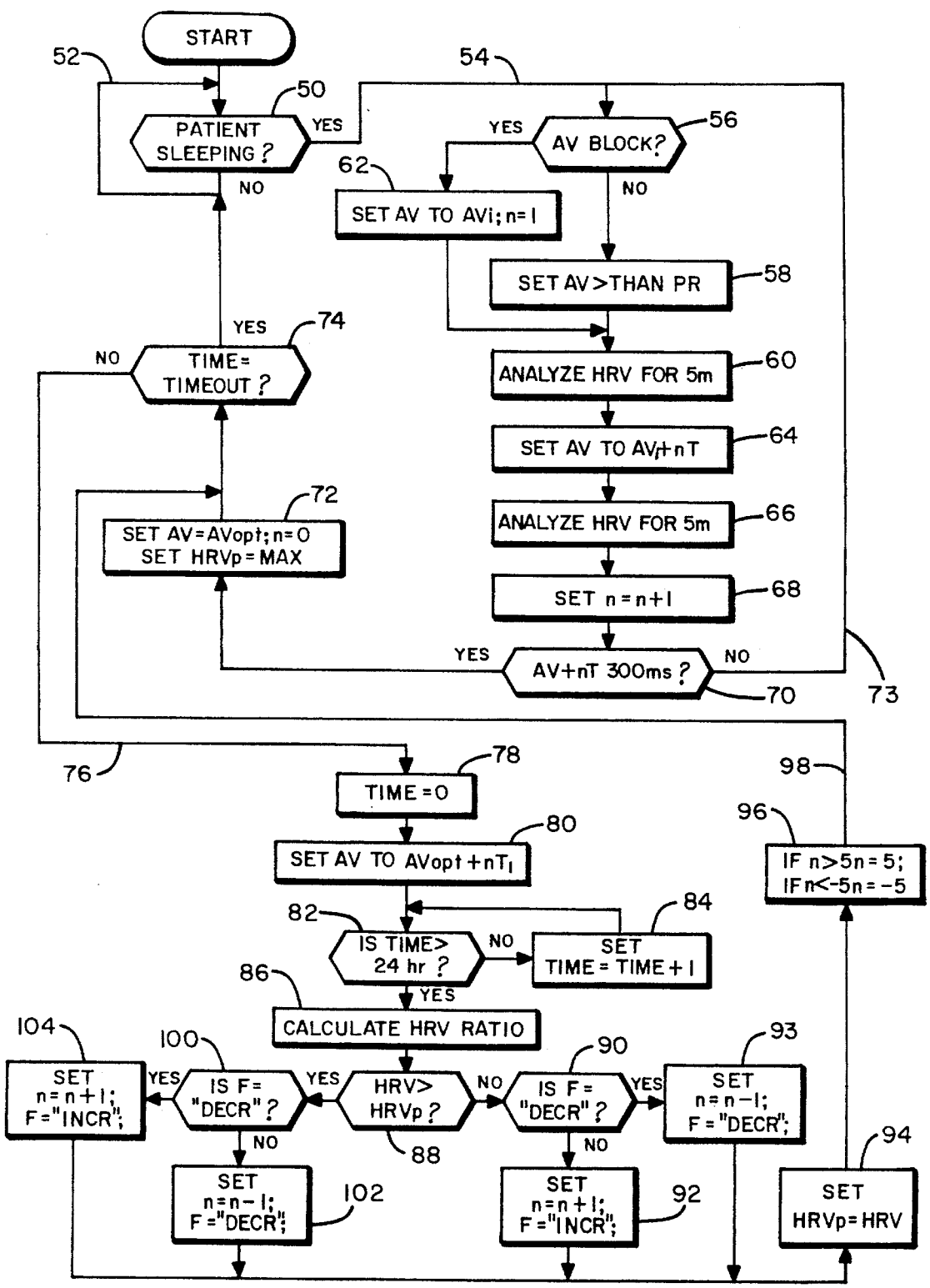
FIG. 4 is a flow diagram of the software executed by the microprocessor-based controller shown in FIG. 2 for automatically maintaining the A-V delay at an optimum value for the particular patient in whom the system is implanted and used.

Referring next to FIG. 4, there is shown a software flow diagram of the algorithm embodied in the microprocessor-based controller 30 for optimizing the A-V interval of a pacemaker based upon derived minimum values of $HRV_i$. The program starts with a first test to determine whether the patient is in a resting state at block 50. Information from the accelerometer 33 contained within the implantable pacemaker 12 is processed to assess the level of physical activity of the patient.

If the patient has been active within a predetermined period of time, control loops back, via path 52, until a determination is made that he/she is asleep and control exits on path 54 where a determination is made at block 56 whether the patient suffers from second or third degree A-V block. If neither type of heart block is present, the programmable controller sets the A-V interval to a value that is greater than the intrinsic PR interval of the heart (block 58) to allow for intrinsic conduction. Next, variations in the R-R interval of the heart are analyzed for a predetermined period, such as five minutes (block 60) and the heart rate variability ratio $HRV_i$ is computed by determining from the FFT derived power spectrum the low frequency power and high frequency power components. The ratio thereof is then formed as is more further explained in the aforereferenced Ori et al. paper. Had it been determined at block 56 that the patient was suffering from second or third degree heart block, the A-V interval for the pacer would be set to a predetermined initial value $A-V_i$ at block 62 before the heart rate variability index was determined at block 60.

Next, the A-V interval of the pacer is set to the initial value $A-V_i$ plus a time increment equal to a count index, n, times a predetermined time increment T. The effect of incrementing the A-V interval from its initial value to the changed value on heart rate variability is again analyzed over a programmable interval, e.g., five minutes, followed by the incrementation of the count index at block 68. Each time a heart rate variability index is computed, it is associated with the particular A-V interval value existing at the time that the $HRV_i$ value in question had been determined. Both of these values are temporarily stored in the RAM memory 38 (FIG. 3).

A test is made at block 70 to determine whether the A-V interval has been incremented to the point where it exceeds a predetermined limiting value, e.g., 300 milliseconds. If not, control returns via path 72 to block 56 followed by the iterative execution of the operations defined by blocks 58–68 until the test at block 70 reveals that the incremented value of the A-V interval reaches 300 milliseconds. At that point, the memory is searched for the A-V interval value associated with the minimum $HRV_i$ value and that A-V delay value is then determined to be optimum and used in controlling the pulse generator 32.

At the same time, the iteration count value, n, is set to zero. Also, a quality $HRV_p$ referring to the immediately preceding computed heart rate variability index is set to its maximum. See operation block 72.

Periodically, it is desirable to repeat the "at rest" optimization sequence just discussed so the algorithm includes the ability to program in a time value measured in units of days, weeks or months, and then that time value is decremented by regularly occurring clock signals from the microprocessor. When the time value is decremented to zero, the "YES" output of block 74 is followed and the previously described A-V interval optimization sequence is again executed.

Assuming that it is not time to repeat the "at-rest" sequence, control out of block 74 follows path 76 and a cycle timer has its contents set to zero as represented by block 78. Next, the A-V interval of the pulse generator is set to the previously determined optimum value established at block 72 plus an increment, nT, at block 80. A test is made at block 82 to determine whether the time value has reached 24 hours and, if not, the time value is incremented at block 84 on repetitive passes until the test at block 82 indicates that a 24-hour interval has expired. When it has, the HRV ratio, determined over the preceding 24-hour period, is calculated in the fashion already described (block 86). That is to say, data is gathered over a 24-hour period relating to cyclic variations in the heart's R-R interval and a frequency domain analysis involving the FFT signal processing is carried out to locate the low frequency and high frequency peaks in the power spectrum. The energy associated with the low frequency peaks is then divided by that associated with the high frequency peaks in arriving at the HRV ratio.

Next, a test is made at block 88 to determine whether the calculated HRV ratio exceeds the previous HRV ratio that had been established at block 72. If it does not, a test is made at block 90 to determine whether a flag bit, F, is set to "decrement". On the first pass through the loop, the answer will be "no" and the value of n of incremented at block 92 and the flag bit, F, is toggled to "increment". Next, the previous heart rate variability index ($HRV_p$) is set equal to the value computed at block 86. See block 94.

The operation performed at block 96 insures that the index value, n, is limited to lie between programmable limits, e.g., ±5. Control then returns via path 98 to block 74.

This sequence is repeated at 24 hour intervals later and a new HRV ratio value is computed each time at block 86 and tested at block 88 to see if the newly computed value is greater than the previous HRV value. Assuming it is not, the result of the test at block 90 on the second pass will again be "NO" because the flag bit, F, had been set to "increment" on the previous pass. The count value, n, will again be incremented and the previous HRV value will be replaced by the just calculated value at block 94. The value of "n" is again tested at block 96 to see if it is within limits. When "n" exceeds its limit (i.e., 5) in the positive direction, on the next pass, "n" at block 11, will be set to its limit rather than any value greater than it.

Let it be assumed that on the next pass, the HRV value calculated at block 86, based upon the new value of the A-V delay entered at block 80, exceeds the previous HRV value. A test at block 100 will result in a "NO" response since on the previous pass, the flag bit, F, was set to "increment" at block 92. As a result, n, will be decremented (block 102) and Flag bit is set to "decrement". Then, the previous value of heart rate variability index, $HRV_p$, is replaced with the newly calculated value. If the new value of n is between the limits (i.e., ±5), that value of n will be used on the next pass.

Next assume that operation continues and a point is reached where the change in the A-V delay interval causes the calculated $HRV_i$ to exceed its previous value and the F bit is set to "decrement". Under these circumstances, control passes to block 104 and the value of n is incremented by one while the Flag bit, F, is set to "increment" prior to $HRV_p$ being set equal to the value calculated at block 86.

It can be seen from the above explanation that at 24-hour intervals, a new A-V delay value ($AV_{opt}+nT$) is used by the pacer and HRV ratio, based on that change, is calculated. If the new value exceeds the previous value, the counter index, n, is decremented so that on the next pass the quantity $(AV_{opt}+nT)$ will be decreased. If on this next pass, the same result occurs, i.e., HRV is greater than $HRV_p$, another decrementation cycle occurs. If a point is reached where further decrementation of the A-V value results in worsened (larger) HRV ratio than on a preceding cycle, then n will again be incremented. Thus, the A-V interval value will oscillate back and forth about an optimum value that yields a minimum HRV ratio.

In another embodiment, the 25-hour optimization period can be an integer number of days, weeks, or even months. In still another embodiment, a measurement of $HRV_i$ during sinus rhythm between two consecutive AV delays or mode changes can be used to obtain a reference $HRV_i$. In this case, the optimum setting would be the one that provides the maximum decrease in $HRV_i$ with respect to the $HRV_i$ obtained during intrinsic sinus rhythm. In case of second or third degree AV block, a standard AV delay and pacing mode can be used for this reference.

A DDD pacemaker having a microprocessor-based controller programmed in accordance with the flow diagram of FIG. 4 allows the optimum A-V delay of the pulse generator to be automatically set without the need for intervention of any external equipment. Furthermore, the approach described can be extended to optimize the pacing mode of such a cardiac rhythm management device. In a DDD or a DDDR pacing system, there are four possible modes of pacing:

(a) sensing in the atrium and sensing in the ventricle;

(b) sensing in the atrium and pacing in the ventricle;

(c) pacing in the atrium and sensing in the ventricle; and (d) pacing in the atrium and pacing in the ventricle.

One of the problems faced by a cardiologist in trying to set the A-V delay of the pacemaker is that the optimum delay is dependent on the current pacing mode. This is due to the fact that it takes a different time for an electrical stimulus to propagate from the right atrium to the left atrium, depending on whether it is a paced beat or a normally generated (sinus node) beat. At the same time, it will take a greater time for an electrical stimulus to propagate from the right ventricle (paced ventricle) to the left ventricle if it is a paced apical stimulus than if it a normal conducted beat (using the specialized conduction system composed by the His bundle and purkinje fibers). The method of the present invention addresses the problem of finding the optimum A-V delay for all of the above pacing modes for a particular patient, by providing the means to compensate for the difference in inter-atrial propagation times that exists between pacing modes (b) and (d) above, by programming the optimum A-V delay with an A-V delay offset. Those skilled in the art will appreciate that the present invention is capable of repeating the above-described procedure for atrial paced beats as well as intrinsic SA node activity and can program into the device the optimum offset between atrial paced and sensed beats. The A-V delay scanning window (0–300 ms) is also programmable and can be divided into time intervals of programmable length, e.g., five milliseconds.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. Cardiac stimulating apparatus for use with a patient comprising, in combination:

(a) means for sensing atrial depolarization signals;

(b) means for sensing ventricular depolarization signals;

(c) means for stimulating ventricular tissue; and (d) microprocessor-based controller means coupled to said means for sensing ventricular depolarization signals for determining a heart rate variability index ($HRV_i$) during a predetermined time interval, said controller means further being coupled to said means for sensing atrial depolarization signals for establishing an optimum A-V delay interval corresponding to a minimum $HRV_i$, said controller means coupled in controlling relation to said means for stimulating ventricular tissue for causing said ventricular tissue to be stimulated in at least one ventricular chamber after expiration of said optimum A-V delay interval following the sensing of an immediately preceding atrial depolarization signal.

2. The cardiac stimulating apparatus as in claim 1 wherein said microprocessor-based controller includes means for determining the said $HRV_i$ from a power spectrum analysis of cyclic variations in the rate at which said ventricular depolarization signals are occurring.

3. The cardiac stimulating apparatus as in claim 2 wherein said $HRV_i$ is the ratio of low frequency power to high frequency power found in said power spectrum analysis.

4. The cardiac stimulating apparatus as in claim 1 wherein said microprocessor-based controller includes means for determining the said $HRV_i$ from the standard deviation of R-R intervals of the heart during a predetermined time interval and respiratory sinus arrhythmia from measured values of mean absolute differences between each R-R interval and a successive one.

5. The cardiac stimulating apparatus as in claim 1 and further including means in said cardiac stimulating apparatus for indicating the activity state of a patient and means responsive to said activity state indicating means for inhibiting the determination of said optimum A-V interval when said patient is awake.

6. The cardiac stimulating apparatus as in claim 3 wherein said microprocessor-based controller is programmed to periodically minimize the patient's $HRV_i$ by controllably modifying said optimum A-V delay interval.

7. The cardiac stimulator as in claim 6 wherein said patient's $HRV_i$ is minimized at a predetermined frequency.

8. The cardiac stimulating apparatus as in claim 7 wherein the frequency at which said $HRV_i$ is minimized is daily.

9. The cardiac stimulating apparatus as in claim 6 wherein the frequency at which said $HRV_i$ is minimized is weekly.

10. The cardiac stimulating apparatus as in claim 6 wherein the frequency at which said $HRV_i$ is minimized is monthly.

11. A method for setting the A-V delay of an implantable DDD pacemaker of the type having a means for sensing atrial events, means for sensing ventricular events, means for stimulating ventricular tissue and a programmable microprocessor-based controller coupled to said atrial and ventricular sensing means and to said means for stimulating ventricular tissue comprising the steps of:

(a) establishing an initial A-V delay interval between the sensing of an atrial event and an actuation of said means for stimulating ventricular tissue;

(b) measuring a heart rate variability index ($HRV_i$) of a patient in whom said pacemaker is implanted for a predetermined period of time following the establishing of each A-V delay interval and determining an average value for said period;

(c) incrementing the length of said initial A-V interval by a predetermined amount during iterative cycles until a predetermined A-V interval limit is reached and for each new value thereof computing $HRV_i$ over a predetermined length of time;

(d) storing said A-V delay interval and the associated $HRV_i$ following each iteration of step (c);

(e) setting said A-V interval to the value associated with the minimum $HRV_i$ stored after said A-V interval limit has been reached.

12. The method as in claim 11 wherein measuring a $HRV_i$ includes the steps of:

(a) measuring an RR interval of the heart over time using said means for sensing said ventricular events and determining a corresponding heart rate value;

(b) performing a power spectrum analysis on the measured heart rate value;

(c) determining from said power spectrum analysis the power associated with low frequency components and high frequency components; and (d) forming the ratio of low frequency power to high frequency power.

13. The method as in claim 11 and further including the step of inhibiting the execution of steps (a)–(e) if said patient is awake.

14. The method as in claim 12 and further including the step of periodically changing the A-V delay interval by a known increment and measuring the effect of such change on the patient's $HRV_i$.

15. The method as in claim 14 and further including the step of determining whether a change in the A-V delay interval causes an increase or a decrease in said $HRV_i$ and subsequently changing the A-V delay interval in a direction to minimize said $HRV_i$.

16. The method as in claim 11 wherein measuring a $HRV_i$ includes the steps of:

(a) measuring an R-R interval of the heart over a predetermined time interval using said means for sensing said ventricular events and determining a standard deviation (SD);

(b) computing a respiratory sinus arrythmia (RSA) value from the mean absolute difference between each R-R interval and a succeeding one; and (c) forming the ratio of SD/RSA.

17. A method of determining the optimum pacing mode for a cardiac stimulator of the type having a means for sensing atrial events, means for sensing ventricular events, means for stimulating ventricular tissue, a means for stimulating atrial tissue and a programmable microprocessor-based controller coupled to said atrial and ventricular sensing means and to said means for stimulating ventricular tissue and said means for stimulating atrial tissue comprising the steps of:

(a) programming the stimulator to operate in a first pacing mode;

(b) thereafter establishing an initial A-V delay interval between the sensing of an atrial event and the actuation of said means for stimulating ventricular tissue;

(c) measuring a heart rate variability index ($HRV_i$) of a patient in whom said cardiac stimulator is implanted for a predetermined period of time following the establishing of each A-V delay interval and determining an average value for said period;

(d) incrementing the length of said initial A-V interval by a predetermined amount during iterative cycles until a predetermined A-V interval limit is reached and for each new value thereof, computing said $HRV_i$ over a predetermined length of time;

(e) storing said A-V delay interval and its associated $HRV_i$ following each iteration of step (d);

(f) determining the average $HRV_i$;

(g) programming the cardiac stimulator to operate in a second pacing mode different from said first pacing mode;

(h) repeating steps b through f;

(i) comparing the average $HRV_i$ computed in step f with that computed in step h; and (j) programming the cardiac stimulator to operate in the mode yielding the minimum average $HRV_i$.

18. The method of determining the optimum pacing mode as in claim 17 wherein said pacing modes are selected from the group including sensing atrial events and sensing ventricular events, sensing atrial events and stimulating ventricular tissue, stimulating atrial tissue and sensing ventricular tissue, and stimulating atrial tissue and stimulating ventricular tissue.

19. The method of determining the optimum pacing mode as in claim 17 wherein measuring a $HRV_i$ includes the steps of:

(a) measuring an R-R interval of the heart over time using said means for sensing said ventricular events and determining a corresponding heart rate value;

(b) performing a power spectrum analysis on the measured heart rate value;

(c) determining from said power spectrum analysis the power associated with low frequency components and high frequency components; and (d) forming the ratio of low frequency power to high frequency power.

20. The method as in claim 17 and further including the step of periodically changing the A-V delay interval by a known increment and measuring the effect of such change on the patient's $HRV_i$.

21. The method as in claim 20 and further including the step of determining whether a change in the A-V delay interval causes an increase or a decrease in said $HRV_i$ and subsequently changing the A-V delay interval in a direction to minimize said $HRV_i$.

22. The method as in claim 17 wherein measuring a $HRV_i$ includes the steps of:

(a) determining the standard deviation (SD) of the R-R intervals of the heart during a predetermined time interval;

(b) determining the respiratory sinus arrhythmia (RSA) from measured values of the mean absolute difference between each R-R interval and the successive one; and (c) computing $HRV_i$ as the ratio equal to SK/RSA.

* * * * *